(12) United States Patent
Holzner et al.

(10) Patent No.: US 8,673,993 B2
(45) Date of Patent: Mar. 18, 2014

(54) METHOD FOR PRODUCING A CROSS-LINKED ELASTOMER

(75) Inventors: Armin Holzner, Ternitz (AT); Wolfgang Kern, Seiersberg (AT); Raimund Schaller, Neunkirchen (AT); Sandra Schloegl, Stallhofen (AT)

(73) Assignee: Semperit Aktiengesellschaft Holding, Vienna (AT)

( * ) Notice: Subject to any disclaimer, the term of this patent is extended or adjusted under 35 U.S.C. 154(b) by 143 days.

(21) Appl. No.: 13/257,184

(22) PCT Filed: Mar. 17, 2010

(86) PCT No.: PCT/AT2010/000081
§ 371 (c)(1),
(2), (4) Date: Nov. 28, 2011

(87) PCT Pub. No.: WO2010/105283
PCT Pub. Date: Sep. 23, 2010

(65) Prior Publication Data
US 2012/0084901 A1    Apr. 12, 2012

(30) Foreign Application Priority Data

Mar. 17, 2009    (AT) .................................. A 421/2009

(51) Int. Cl.
*C08F 2/46*     (2006.01)
*C08G 61/04*    (2006.01)

(52) U.S. Cl.
USPC .................................................. 522/1; 520/1

(58) Field of Classification Search
USPC .................................................. 522/1; 520/1
See application file for complete search history.

(56) References Cited

U.S. PATENT DOCUMENTS

| 6,329,444 | B1 | 12/2001 | McGlothlin et al. |
| 2003/0141457 | A1 | 7/2003 | Nakagawa et al. |
| 2003/0195273 | A1* | 10/2003 | Mitra et al. .................. 523/120 |
| 2006/0229377 | A1 | 10/2006 | Bublewitz et al. |
| 2007/0105971 | A1* | 5/2007 | Schaller et al. .............. 521/84.1 |
| 2009/0186164 | A1* | 7/2009 | Hirao et al. .................. 427/516 |

FOREIGN PATENT DOCUMENTS

| AT | 502764 | 5/2007 |
| DE | 10 2005 016762 | 10/2006 |
| DE | 10 2005 043222 | 3/2007 |
| EP | 0 856 294 | 9/1997 |
| EP | 1 762 586 | 3/2007 |
| GB | 2 239 247 | 6/1991 |

OTHER PUBLICATIONS

Search report from International Application No. PCT/AT2010/000081, mail date is Feb. 7, 2010.

* cited by examiner

*Primary Examiner* — Ling Choi
*Assistant Examiner* — Jessica E Whiteley
(74) *Attorney, Agent, or Firm* — Greenblum & Bernstein, P.L.C.

(57) ABSTRACT

The invention relates to method for producing a crosslinked elastomer by radiating a polymer dispersion of at least one crosslinkable polymer with electromagnetic radiation in the ultraviolet (UV light) and/or visible spectral range, wherein the crosslinking is performed in at least two stages as pre-crosslinking and post-crosslinking and at least one photoinitiator is added to the polymer dispersion to trigger the crosslinking reaction prior to the pre-crosslinking. At least one photoinitiator is added once again to the pre-crosslinked polymer dispersion prior to and/or during the post-crosslinking, and the post-crosslinking is also performed with electromagnetic radiation in the ultraviolet (UV light) and/or visible spectral range.

28 Claims, 3 Drawing Sheets

METHOD FOR PRODUCING A CROSS-LINKED ELASTOMER

The invention relates to a method for producing a crosslinked elastomer by radiating a polymer dispersion consisting of at least one crosslinked polymer with electromagnetic radiation in the ultraviolet (UV-light) and/or visible spectral range, wherein the crosslinking is performed in at least two stages as pre-crosslinking and post-crosslinking, and at least one photoinitiator is added to the polymer dispersion for triggering the crosslinking reaction prior to the pre-crosslinking, a method for producing an immersion article made of at least one latex, in particular a glove or a condom, in which a mold with an external contour which corresponds to the immersion article to be produced is immersed for a prespecifiable period in an immersion bath, containing the at least one latex, and afterwards the immersion article is hardened and/or dried, a device for producing an immersion article made of a latex, comprising a reactor, at least one immersion mold and at least one immersion bath, wherein at least one first radiation source is assigned to the reactor for emitting electromagnetic radiation in the ultraviolet (UV-light) and/or visible spectral range, and a glove made from a crosslinked elastomer.

In order to give elastomers the specific elastic properties, the polymer chains of the elastomer have to be cross-linked at least partially. Usually the crosslinking is performed via double bonds, which are located either in the main chain of the elastomer, such as for example with polyisoprene, polybutadiene, styrene-butadiene-rubber, chloroprene, nitrile-butadiene-rubber, or a side chain, such as e.g. with EPDM. On a large scale the crosslinking of elastomers, including rubber latex, has been performed previously on three different types, namely by sulfur crosslinking, peroxide crosslinking or by radiation crosslinking methods.

From document EP 1 762 586 A2 belonging to the applicant a method for producing gloves by means of the UV crosslinking of a rubber is also known. In addition, the latex is exposed to UV radiation in a falling film reactor and afterwards the gloves are immersed in the usual manner. In this way also the option of post-crosslinking is addressed, but not explained in more detail. It is an advantage in this case that no conventional process chemicals have to be used, such as e.g. the mentioned organosulfur compounds, wherein the potential of contact allergies from such gloves can be reduced.

The objective of the present invention is to improve this UV crosslinking method further.

Said objective of the invention is achieved—independently respectively—in that in the method according to the invention at least one photoinitiator is added once again to the pre-cross-linked polymer dispersion prior to and/or during the post-crosslinking and the post-crosslinking is also performed with electromagnetic radiation in the ultraviolet (UV light) and/or visible spectral range, in that also in the method for producing an immersion article the latex is cross-linked according to this method, in that in the device after the at least one immersion bath an additional radiation source is arranged for the emission of electromagnetic radiation in the ultraviolet (UV light) and/or visible spectral range, and by the glove which is produced according to this method and has a tearing resistance of at least 14 N/mm$^2$, in particular at least 20 N/mm$^2$, preferably at least 25 N/mm$^2$.

Surprisingly, it has been found that by dividing the UV crosslinking into two individual cross-linking stages, namely the pre-crosslinking and the post-crosslinking, wherein both partial crosslinkings are performed by means of radiation in the UV and/or VIS range, the mechanical strength of the elastomer films, in particular the tearing resistance, can be improved compared to single radiation with UV light. In addition, by means of this division an improved process guiding can be achieved for producing gloves, in that the film formation can be improved in the pre-crosslinking stage. As before, the products produced thereby, for example examination gloves, operation gloves, condoms, catheters, infusion tubes, anesthesia masks, etc., have a low allergy potential and not a type IV allergy potential. In addition, the ageing resistance of the elastomer can be improved. Also with regard to high-energy radiation the elastomer products have an improved stability. This is important in particular with regard to the sterilization of the medical products with gamma radiation. In addition, by means of this division of the crosslinking the total energy consumption can be reduced significantly, which solely owing to the fact that the UV crosslinking can occur at room temperature, is already lower than in alternative crosslinking methods. Furthermore, by means of the post-crosslinking possibly available concentrations of residual chemicals can be reduced by covalent bonding of the residual chemicals on the latex. By means of the higher tearing strengths of the films the latter can be produced with a smaller wall thickness, whereby the operating efficiency of the method can be improved.

According to one embodiment variant, the added amount of the at least one photoinitiator in the pre-crosslinking is the same size at most, preferably smaller than the amount of the at least one photoinitiator, which is used for the post-crosslinking. In this way the formation of a film e.g. on the glove mold during the immersion method can be improved, as in the pre-crosslinking an intermediate product is produced, the mechanical strength of which is still much lower than that of the end product, in particular owing to the smaller number of crosslinking points, and thus the flow behavior of the latex or gel has a positive effect on the particularly even film formation.

However, it should be noted that the added amount of photoinitiator or photoinitiators in the pre-crosslinking is greater than in the post-crosslinking, even though the aforementioned embodiment variant is preferred.

In particular, it has proved to be advantageous for the production of medical latex products, in particular gloves, for the crosslinking reaction of the latex or the latex mixture with regard to balanced mechanical properties, in particular a desired strength with a corresponding relaxation of the glove, i.e. reduction of the pressure or force on the hand after the expansion caused by pulling on the glove and thus avoiding a "feeling of constriction" of the wearer or in order to ensure a suitable level of tactility for the glove wearer, if the proportion of the at least one photoinitiator at the polymer dispersion for the pre-crosslinking is between 0.2 phr and 5.0 phr or if according to a further embodiment variant the proportion of the at least one photoinitiator at the polymer dispersion for the post-crosslinking is between 0.5 phr and 5.0 phr. Below the lower limit values the crosslinking for the desired mechanical properties is too low. Concentrations of more than 5.0 phr for the pre- or post-crosslinking have a negative effect on the economic efficiency of the method and also the crosslinking density is too great.

To improve the tearing resistance and also for reasons of economic efficiency it is also an advantage if the proportion of the at least one photoinitiator at the polymer dispersion for the pre-crosslinking is between 0.5 phr and 3.5 phr, in particular between 0.75 phr and 1.2 phr, or if according to a further embodiment variant the proportion of the at least one photoinitiator at the polymer dispersion for the post-crosslinking is between 0.8 phr and 3.75 phr, in particular between 1 phr and 1.5 phr.

Preferably the polymer dispersion in the pre-crosslinking is radiated at least twice. Surprisingly, the finished elastomer after double or triple radiation has more homogenous properties, such as e.g. mechanical tearing resistance. In addition, the device according to the invention can have two or three reactors in flow direction of the latex arranged behind one another, in order to enable continuous production. In experiments with four or more exposure cycles it was found that the tearing resistance of the finished product does not change so much that the economic efficiency of the method is reduced. In addition, possibly also an over-crosslinking in the pre-crosslinking phase can be observed. With a single radiation the tearing resistance by a lower pre-crosslinking can also be lower.

Preferably, a photoinitiator is used, which is selected from a group comprising 2-hydroxy-2-methyl-1-phenylpropanone (trade name: Genocure DMHA; Rahn AG), phenylglyoxylic acid methyl ester, 2,4,6-trimethylbenzoylphenylphosphinic acid ethyl ester (trade name: Lucirin TPO L; BASF), methylbenzoylformiate (trade name: Genocure MBF; Rahn AG), 1-[4-(2-hydroxyethoxy)-phenyl]-2-hydroxy-methyl-1-propanone-1-one (trade name: Irgacure 2959; Rahn AG) 2-dimethylamino-2-(4-methylbenzyl)-1-(4-morpholine-4-ylphenyl)-butane-1-one (trade name: Irgacure 379; CIBA), 2 methyl-1-[4-(methylthio)phenyl]-2-morpholinopropane-1-one (trade name: Irgacure 907; CIBA), 2,4,6-trimethylbenzoyldiphenylphosphine oxide (trade name: Lucirin TPO; BASF). On the one hand its good skin tolerance is advantageous as well as its harmlessness with regard to food, so that if small amounts remain in the finished elastomer, no problems arise, whereby the production i.e. the washing steps can be simplified. In addition, said photoinitiators have a high reactivity, so that an efficient crosslinking can be performed at a lower radiation output or lower photoinitiator concentration, whereby also the processing costs can be reduced. In addition, said photoinitiators have a high thermal stability. Lucirin TPO (L) and Genocure DMHA also have the advantage that the latter are available in liquid form and thus can be emulsified more easily with additional process chemicals, such as e.g. stabilizers, in aqueous systems. In addition, the absorption range of Lucirin TPO L extends to over 400 nm, so that longer wave light can be used for the radiation. This has the advantage however that the radiation can also penetrate into lower layers. In this way thicker walled or heavily pigmented elastomer films or products can be produced.

According to one embodiment variant of the invention the pre-crosslinking is performed on a film, in particular if natural rubber is crosslinked. Preferably, the layer thickness is between 0.1 mm and 2 mm. In this way also latex types can be processed continually which have a high or higher absorption. By means of the low layer thickness during the pre-crosslinking the layer to be radiated can be penetrated almost homogenously.

In particular, the layer thickness of the film during the pre-crosslinking is between 0.3 mm and 0.6 mm.

By means of the use of at least two radiation sources in the post-crosslinking more homogenous dose distributions can be achieved with three-dimensionally shaped products, such as e.g. gloves, also on a large technical scale. For example between three and eight, in particular six radiators are arranged in production direction behind one another in the device. Of course, also more than eight radiators can be provided.

It is also an advantage if the post-crosslinking is performed with a higher radiation dose than the pre-crosslinking. In this way in the pre-crosslinking lower crosslinking levels are made possible, whereby the film formation can be improved, e.g. on an immersion mold, in that the latex particles flow better into one another and can fuse together, and the higher tearing resistances can be achieved as a result by the higher radiation dose in the post-crosslinking.

In this case it is an advantage in particular, for example for the crosslinking of IR latex, if the post-crosslinking is performed by a radiation dose, which is between 150% and 500% of the radiation dose of the pre-crosslinking.

Preferably, the post-crosslinking is performed with a radiation dose, which is between 200% and 300% of the radiation dose of the pre-crosslinking.

For the pre-crosslinking and/or the post-crosslinking at least one co-crosslinker with at least one thiol group is added to the latex or the pre-crosslinked latex. In this way the sequence of the crosslinking is possible via a (radical) thiol-ene reaction, whereby the oxygen inhibition of the crosslinking can be reduced so that crosslinking can be performed in air. In addition, the gel point is delayed, whereby a higher crosslinking and thereby a higher mechanical tearing resistance can be achieved.

For the aforementioned reasons regarding the amount ratios of the photoinitiator in the pre-crosslinking and the post-crosslinking it is an advantage if the added amount of the at least one co-crosslinker in the pre-crosslinking are the same size, preferably smaller than the amount of the at least one co-crosslinker, which is used for the post-crosslinking, wherein the proportion of the at least one co-crosslinker on the polymer dispersion for the pre-crosslinking is preferably between 0.5 phr and 2.0 phr and the proportion of the at least one co-crosslinker at the polymer dispersion for the post-crosslinking is between 0.5 phr and 2.5 phr.

To improve the tearing resistance and also for economic reasons it is also an advantage if the proportion of the at least one co-crosslinker at the polymer dispersion for the pre-crosslinking is between 0.1 phr and 1.5 phr or between 0.2 phr and 1.2 phr, and if according to a further embodiment variant the proportion of the at least one co-crosslinker on the polymer dispersion for the post-crosslinking is between 0.9 phr and 2 phr or between 1.2 phr and 1.5 phr.

Preferably as the co-crosslinking agent trimethylolpropane-tris-3-mercaptopropionate or pentaerythritol tetrakis-3-mercaptopropionate is used, as the latter have a relatively high reactivity, wherein trimethylolpropane-tris-3-mercaptopropionate has a higher reactivity than pentaerythritol tetrakis-3-mercaptopropionate, pentaerythritol tetrakis-3-mercaptopropionate however has the advantage that it is allowed to be in contact with foodstuffs. In addition, pentaerythritol tetrakis-3-mercaptopropionate has the advantage that the risk of over crosslinking is ritol tetrakis-3-mercaptopropionate has the advantage that the risk of over crosslinking is lower so that in this way also a third exposure cycle in the pre-crosslinking is possible. With the use of two exposure cycles however the use of trimethylolpropane-tris-3-mercaptopropionate had advantages over the use of pentaerythritol tetrakis-3-mercaptopropionate, whereby in principle the use of both co-crosslinking agents is possible, also at the same time.

Surprisingly, at least one ageing protection agent can be added to the pre-crosslinked polymer dispersion prior to the post-crosslinking, whereby not only can the resistance to ageing itself be improved, but it is also possible in this way to improve the resistance of the elastomer to high-energy radiation, such as e.g. for sterilization.

As ageing protection agents in particular vitamin E and/or sterically hindered phenolic compounds can be used, such as e.g. butylated reaction products of p-Cresol and dicyclopentadiene (RALOX® LC, Fa. Solvadis). Vitamin E ($\alpha$-tocopherol) is a known radical scavenger. In addition, it has the advantage that with respect to human tolerance it is harmless, so that also an additional benefit for the user of the finished elastomer articles, for example gloves, can be obtained. Vitamin E also has the advantage however that it only slightly inhibits the thiol-ene reaction.

To increase the efficiency of the post-crosslinking it is an advantage if between the pre-crosslinking and the post-crosslinking the pre-crosslinked elastomer is dried up to a residual moisture of a maximum of 6%. In this way the light scattering of the latex film is reduced, so that the excitation light can penetrate into deeper layers.

To improve this effect further and thus to increase the tearing resistance further it is an advantage if the drying is performed up to a residual moisture content of a maximum of 4%, relative to the film.

Prior to the pre-crosslinking at least one surfactant with at least one photochemical active center can be added to the polymer dispersion, in particular with a double bond, e.g. linoleic acid, in order to improve the film formation of the latex.

For crosslinking, in particular post-crosslinking, for radiation a mercury high pressure vapor lamp doped with gallium can be used. By means of the gallium doping a shifting of the emission range of the lamp to longer wavelengths is achieved, which can extend into the visible range. In this way also deeper layers of the latex can be cross-linked more effectively, in particular with the use of Lucirin TPO L. It has also been shown that the surface of the latex film is damaged less by an ozone attack, so that the resistance to ageing can be improved further.

It is also possible that the post-crosslinking is performed in an inert gas atmosphere, for example argon or nitrogen, in order to avoid a worsening of the surface properties by the influence of oxygen.

The shaping of the latex by immersing the mold into the immersion bath can be performed in the method of producing an immersion article between the pre-crosslinking and the post-crosslinking of the latex, whereby better film qualities are achieved.

It is an advantage in this case if the post-crosslinking is performed on the mold, i.e. the film is located on the mold during the post-crosslinking. Although homogenous radiation is made more difficult in this case, this procedure has the advantage than the films do not have to be removed from the molds, so that on the one hand the economic efficiency of the method can be improved, and on the other hand problems with the handling of sticky films can be avoided. It has proved to be advantageous if the mold is aligned during the post-crosslinking at different angles to the radiation source. In this way the homogeneity of the radiation can be improved, in particular shadowing effects can be avoided more effectively owing to the three-dimensionality of the product.

According to one embodiment variant of the device, a rolling unit is arranged after the at least one immersion bath, by means of which the immersion articles can be rolled at least partly, in particular with gloves on the open end of the shaft, and in that the additional radiation source is assigned to the rolling unit. In this way it is achieved that the immersion mold and the elastomer film located thereon are radiated not only during the translatory advance movement but that a rotational movement is superimposed over the translatory movement, whereby the radiation of the elastomer film, in particular the dose distribution can be performed more homogenously over the glove surface. The speed of the translatory advance movement can in this case be between 1 m/min and 25 m/min, that of the rotation movement between a 25 U/m feed rate and 50 U/m feed rate.

For the aforementioned reasons for the pre-crosslinking preferably at least two reactors are arranged behind one another in the device with respectively at least one first radiation source in production direction.

Between the two reactors of the device at least one container can be arranged, which possibly comprises an agitator. It is thus possible in a simple manner to subsequently dose or add process chemicals between the two exposure cycles.

It should be noted at this point that also additional reactors can be used, e.g. a third reactor, in order in a continual reaction guiding to perform the cleaning of one of the two other reactors.

It is possible to use a spectral range for the crosslinking with wavelengths selected from a range with a lower limit of 150 nm, in particular 250 nm, preferably 275 nm, and an upper limit of 600 nm, in particular 475 nm, preferably 400 nm.

In addition to the aforementioned photoinitiators in principle also other photoinitiators can be used, which in the ultraviolet and/or visible spectral range, in particular in the blue range of the visible spectral range adjoining the UV range, exhibit a corresponding reaction. Examples of this are included in the aforementioned EP 1 762 586 A2, which in this connection belongs to the content of the present invention.

In addition to the preferred co-crosslinking agents mentioned above also other co-crosslinking agents can be used in order to improve the crosslinking. For example, also at least one selenol can be used as the co-crosslinking agent, such as e.g. 1,6 hexane diselenol, or other thiols, in particular multifunctional compounds or derivatives thereof, such as e.g. bis-thiols, for example 1,6-hexane dithiol, tristhiols, bis-selenols, tris-selenols, as well as mixtures thereof.

In the method according to the invention at least one additional auxiliary agent can be used, selected from a group comprising, in particular multifunctional, acrylates, such as e.g. hexane dioldiacrylate (HDDA), trimethylolpropane triacrylate (TMPTA), compounds with vinyl or allyl groups, such as e.g. triallyl-cyanurate, triallyl-isocyanurate, as well as mixtures thereof, such as e.g. at least one mentioned, in particular multifunctional acrylate with at least one said compound with vinyl or allyl groups, in order thus to improve the crosslinking behavior, whereby in turn multifunctional compounds are preferred. Such crosslinking (auxiliary) agents can be included in a proportion of up to 10 phr in the polymer dispersion for the pre-crosslinking and/or in the polymer dispersion for the post-crosslinking.

It is also possible to add at least one sensitizer in order to transfer the light energy more effectively onto the photoinitiator and thus accelerate the crosslinking reaction as a whole or have a positive influence on the sequence or in order thereby to made it possible to use photoinitiators which absorb in a different absorption range than would be advantageous for the desired reaction.

The at least one sensitizer can be selected from a group comprising organic dyes such as eosin, aromatic ketones, such as for example benzophenone or thioxanthone, condensed aromatic compounds, such as for example anthracene or chrysene, inorganic pigments such as zinc phthalocyanine or titanium oxide, as well as mixtures thereof, as said compounds, in particular with the used photoinitiator(s), exhibit a suitable interaction.

The proportion of sensitizers is preferably in a range with a lower limit of 0.1% and with an upper limit of 50% of the amount of photoinitiator, or a range with a lower limit of 10% and with an upper limit of 40% of the amount of photoinitiator or a range with a lower limit of 15% and an upper limit of 25% of the amount.

The at least one photoinitiator and/or the at least one co-crosslinking agent and/or the at least one sensitizer can be pre-emulsified or predispersed prior to addition to the at least one latex into a pre-emulsion or pre-dispersion, and for this purpose, in order to improve the dispersing or emulsion behavior of these components, at least one emulsifier or at least one dispersing agent can be added, wherein as the emulsifier or dispersing agent particularly preferably a surfactant is used, in particular polyethylene glycol-sorbitan-monolaurate. In this way the input of said components into the, in particular liquid, latex phase is simplified and in this way also an "equal distribution" of these components in the whole liquid phase can be achieved, whereby higher reaction speeds, i.e. higher conversions per time unit, and thereby a shortening of the method can be achieved.

Said pre-emulsion or pre-dispersion can be added to the latex or latex mixture at least partly prior to the crosslinking reaction. Similarly, it is possible to add the latter at least partly during the crosslinking reaction or between the exposure cycles of the pre-crosslinking. In this way the crosslinking behavior, in particular the start of the crosslinking reaction, of different latex types can be reacted to accordingly and the use of auxiliary components or starter components can be adjusted more effectively to the respectively desired level of crosslinking. In particular, thus also the level of crosslinking of the latex or the latex mixture can be adjusted more effectively.

The at least one latex to be cross-linked according to the invention can be selected from a group comprising natural rubber (NR), polyisoprene-latex (IR), nitrile butadiene rubber latex (NBR), chloroprene-latex (CR), styrene-butadiene latex (SBR), lattices of ethyl acrylate copolymers (ACM), lattices of elastomers which are produced by re-emulsifying, lattices of functional copolymers, such as e.g. photoinitiator-containing and/or carboxylated lattices produced from polymer blends, as well as mixtures thereof, wherein with said lattices—although the use of the method according to the invention does not exclude other latex types with un-saturated C—C bonds—surprisingly good mechanical properties or correspondingly good properties could be achieved.

In this case it is an advantage if a latex is cross-linked with a solids content, which is selected from a range with a lower limit of 20% and an upper limit of 60%, in particular if a latex is crosslinked with a solids content, which is selected from a range with a lower limit of 30% and an upper limit of 50%, preferably if a latex is crosslinked with a solids content, which is selected from a range with a lower limit of 35% and an upper limit of 45%, as with said solids content(s) a suitably good mixing of the individual educts and thus a rapid reaction sequence is possible. In addition, this makes it possible to prevent the layer thickness in the reactor of the pre-crosslinking varying, in particular if a falling film reactor is used, over the length of the radiation. Above a solids content of the latex of 60% the latex becomes too viscous and already tends to coagulate. Below 20% the solids content is too low to form a desired layer thickness during the coagulation immersion process.

Preferably, the crosslinking reaction is performed in a falling film reactor or in an immersion reactor, to enable at predeterminable layer thicknesses of the reaction mixture the application of energy as far as possible into the core areas of the mixture.

As an energy source for electromagnetic radiation in addition to the aforementioned preferred doped mercury vapor lamp also other mercury lamps can be used (pulsed) xenon lamps, an excimer lamp, a laser, such as e.g. an excimer laser or for at least partial crosslinkings in the visible blue range a laser, an LED light source. Likewise microwave excited UV radiators can be used.

To increase the conversion or to increase the specificity of the reaction further, monochromatic radiation can be used and lasers are used in particular for this.

As already mentioned, particularly preferably the crosslinking method for producing a medical glove or an operating glove is used. In particular, in this way also a nitrosamine-free glove can be produced advantageously, made in particular of natural rubber.

The photoinitiator and/or fission products from the reaction can be bonded covalently to the elastomer molecules, whereby the effect of a possible migration of these molecules from the glove can be reduced further.

It is also possible that on the elastomer molecules at least one crosslinking auxiliary means, in particular a multifunctional thiol, is immobilized, in particular bonded covalently, in order to minimize further the risk of skin irritation when using a glove.

The glove according to the invention can be produced to be free of nitrosamine and/or free of accelerators and/or free of sulfur, where free of sulfur is defined to mean that no free sulfur is present, as used for sulfur crosslinking.

For a better understanding of the invention the latter is also explained in more detail with reference to the following Figures.

In a schematically much simplified representation:

Figure 1:
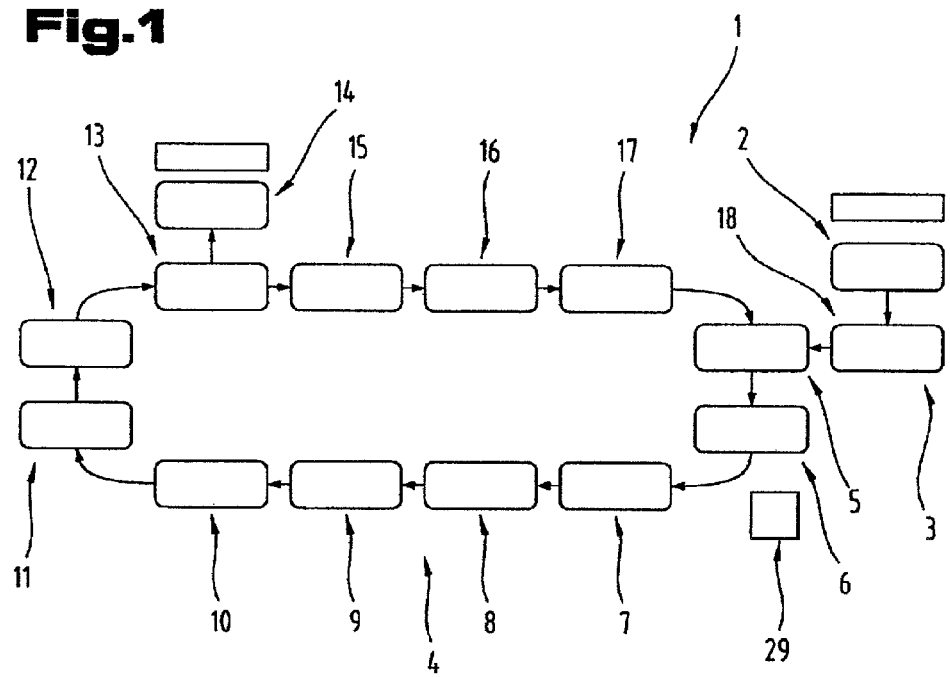
FIG. 1 shows a sequence for the production of powdered operating gloves.

It should be noted that in the variously described exemplary embodiments the same parts have been given the same reference numerals and the same component names, whereby the disclosures contained throughout the entire description can be applied to the same parts with the same reference numerals and same component names. Also details relating to position used in the description, such as e.g. top, bottom, side etc. relate to the currently described and represented figure and in case of a change in position should be adjusted to the new position. Furthermore, also individual features or combinations of features from the various exemplary embodiments shown and described can represent in themselves independent or inventive solutions.

All of the details relating to value ranges in the present description are defined such that the latter include any and all part ranges, e.g. a range of 1 to 10 means that all part ranges, starting from the lower limit of 1 to the upper limit 10 are included, i.e. the whole part range beginning with a lower limit of 1 or above and ending at an upper limit of 10 or less, e.g. 1 to 1.7, or 3.2 to 8.1 or 5.5 to 10.

FIG. 1 shows an embodiment variant of a schematic sequence for producing operation gloves made of latex by immersion in an installation 1.

It should be noted that the invention is not restricted to the production of operating gloves, but rather is aimed in general at cross-linked elastomers, in particular the aforementioned products. In addition to gloves also other latex products can be produced according to the invention, such as for example condoms, various medical latex products, such as for example catheters, diaphragms, infusion bags, medical tubes, tissue culture vessels, etc. or also latex products in the consumer goods field, such as e.g. flippers, pacifiers, etc.

In a mixing step 2 the chemicals necessary for a prevulcanization step 3 are mixed into the latex and if necessary there is a homogenization of the latex. The compounded latex is then pre-vulcanized in the pre-vulcanization step 3. Then the pre-vulcanized latex is transferred into a chain immersion installation 4, where it or the semi-finished product passes through the stages of immersion 5, edging 6, wet-leaching 7, drying 8, possibly dry-leaching 9, possibly powdering 10, removal 11, packaging 12, quality control 13 and possibly sterilization 14. The immersion molds are subjected to cleaning 15, coagulant immersion 16 and drying 17 prior to the repeated immersion in latex.

The immersion molds are usually made of porcelain, but can also be made of glass, stainless steel or plastic. A clean surface for this immersion mold is a criterion for the homogenous deposition of the latex film in the subsequent immersion process. Both alkali and acid solutions, oxidating compounds, surfactants or also often a combination of these cleaning chemicals is used for the degreasing and cleaning of the immersion molds.

The composition of the coagulation bath is also a parameter for the layer thickness of the deposited latex film. The coagulation bath is composed of the coagulants (usually $CaNO_3$, optionally also $CaCl_2$), the releasing agent ($CaCO_3$) and the wetting agent (cationic surfactants). The releasing agent facilitates the removal of the glove from the immersion mold, whereby in separate powder-free processes other inorganic salts and partly also polymers can be used, as is known from the prior art.

The deposited positive metal ions on the surface of the immersion mold bring about a discharge and then the coagulation of the negatively stabilized NR latex, as soon as the mold is immersed into the pre-crosslinked latex. Depending on the immersion period and the concentration of the metal ions different film thicknesses are obtained.

Gloves are produced with a rolled edge on the lower shaft end. For this purpose a portion of the deposited film with edges 6 is rolled together mechanically by rotating brushes. Owing to the stickiness of the film the rolled beaded edge is retained during the entire production process.

The wet latex film is given mechanical strength by a short drying period before wet leaching 7 is performed. By immersing the latex films into a warm water bath in addition to the coagulants ($CaNO_3/CaCl_2$) also proteins are washed out at least partly.

To produce powder-free gloves instead of the powdering 10 a surface treatment can be provided, e.g. by chlorination, in order to improve the ability to put on and remove the gloves. Lubricant coatings are also possible however.

Figure 4:
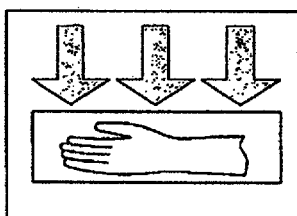
FIG. 4 shows an embodiment variant of the arrangement of the radiation units for the post-crosslinking.
Figure 5:
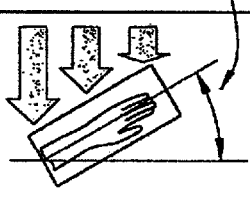
FIG. 5 shows an embodiment variant of the arrangement of the radiation units for the post-crosslinking.

As immersion processes for gloves are known from the prior art, a person skilled in the art is referred for example to EP 0 856 294 A, in particular FIGS. 4 and 5 of said EP-A as well as the relevant explanations in column 14, line 38 to column 18, line 51, in particular in relation to explanations relating to coagulation, immersion in latex, various washing processes, various post-treatments, such as e.g. chlorinating or halogenation of the surface of the gloves or the latex, the roughening of the surface or the provision of powderless gloves etc. In this way unnecessary repetition of the prior art in connection with the present invention is avoided and therefore EP 0 856 294 A1 forms at least in the said scope a part of the disclosure of the present application.

Figure 2:
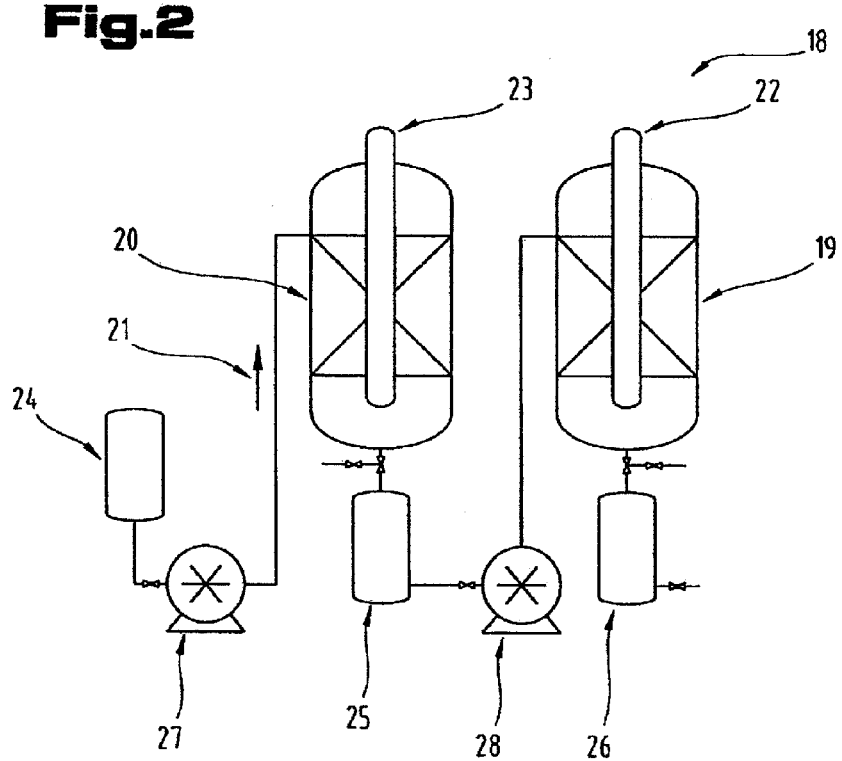
FIG. 2 shows a device according to the invention for pre-crosslinking with a double exposure cycle.

FIG. 2 shows a preferred embodiment variant of a pre-crosslinking device 18. The latter is arranged in the installation according to FIG. 1 between the mixing step 2 and the immersion 5, wherein the pre-crosslinking device 18 can also include the mixing step 2.

In this variant the pre-crosslinking device 18 comprises two reactors 19, 20, in particular falling film reactors, which are connected behind one another in the flow direction of the latex—arrow 21, so that the latex runs through two exposure cycles in the pre-crosslinking, i.e. is exposed to twice the radiation with UV and/or VIS light. In the reactors 19, 20 in addition radiation sources 22, 23 are arranged, in particular Hg high pressure vapor lamps. Before and/or between and/or after the reactors 19, 20 additional containers can be arranged, for example three containers 24, 25 and 26 as in the case of the embodiment variant according to FIG. 2. Said containers can for example be used for dosing (additional) process chemicals, for example the photoinitiator and/or co-crosslinking agent, or as an intermediate storage container for the mixed or pre-cross-linked latex. Furthermore, it is possible that in said container(s) 24, 25 the photoinitiator is laid in a pre-emulsion or pre-dispersion, possibly with a corresponding emulsifying agent. For example surfactants can be used, as already mentioned, as the emulsifying agents.

Furthermore, at least one conveying device 27 can be provided, by means of which the latex is conveyed by the pre-crosslinking device 18. In the embodiment according to FIG. 2 a second conveying device 28 is provided for this, which is arranged in flow direction—arrow 21—between the two reactors 19, 20. For example the conveying devices 27, 28 are formed by eccentric worm pumps.

For the control and/or regulation also suitable controllers, valves, etc. can be arranged on the corresponding points.

Said reactor cascade according to FIG. 2 has the advantage that the two-stage pre-crosslinking of the latex can be performed continually. However, it is also possible to perform said pre-crosslinking with only one reactor 19, for which reason the latex then has to be guided in a circuit in order to enable multiple exposure.

Instead of falling film reactors for example also immersion reactors can be used into which the radiation source 23 immerses.

Figure 3:
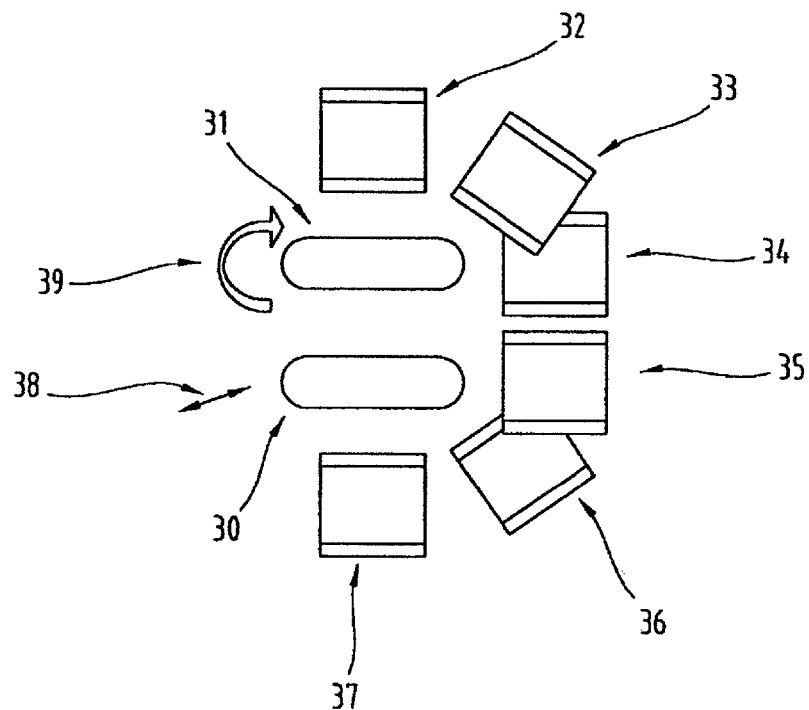
FIG. 3 shows the arrangement of several radiation units for the post-crosslinking of the latex on the mold.

FIG. 3 shows schematically an embodiment variant of a post-crosslinking device 29. Two immersion molds 30, 31 are shown as well as six radiation units 32 to 37. Preferably, this post-crosslinking unit 29 is arranged in the region of the edges 6 of the installation 1 (FIG. 1), as in the case of producing gloves a rotational movement—arrow 39—is superimposed over the translatory forwards movement—arrow 38 in this arrangement, whereby the radiation can be made more consistent, in particular "shaded" areas in the fingers can be better illuminated.

In general. it should be noted that the post-crosslinking device 29 does not necessarily have to be arranged in this position in the installation 1 (FIG. 1), but also can be placed at a different point after the immersion 5 or the shaping of the latex. Also six radiation units 32 to 37 do not have to be used, but also only one radiation unit 32 can be used, in particular for products with a simple geometry, for example with flat films, or a number other than six, for example two, three, four, five, seven, etc.

Preferably, as radiation units 32 to 37 for the above reason Ga-doped Hg-high pressure vapor lamps can be used again. However, also other UV or UV/VIS radiators can be used, for example those mentioned above.

If the post-crosslinking device is situated 29 at a different position in a production installation of crosslinked elastomer (products), it is also possible to provide an additional rotational direction in order to homogenize the radiation.

Preferably, prior to immersion 5 and after the pre-crosslinking device 18 in the installation 1 (Fig.) a drying unit, for example a drying cabinet or hot air furnace, is arranged (not shown), as during the development of the invention it was established that higher tearing resistances can be achieved, if the content of residual moisture is at a maximum at the aforementioned levels.

Figure 6:
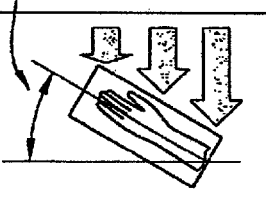
FIG. 6 shows an embodiment variant of the arrangement of the radiation units for the post-crosslinking.

FIGS. 4 to 6 show different options of radiation of immersion molds 30 provided with a latex film 30. Thus in FIG. 4 radiation at a right angle is shown, wherein FIGS. 5 and 6 show radiation at an angle 40 of 30°. To form the angle 40 the immersion mold 30 is inclined accordingly relative to the reference plane (the horizontal in the example according to FIGS. 5 and 6).

By way of dose measuring strips, which were arranged at different points of the hand shape (both on the intermediate spaces between the fingers and on the hand surface), it could be found that even with a simple illumination perpendicular to the hand shape (FIG. 4) also critical areas can be illuminated, wherein the dose distribution in this case is in the region of 1:6 (see table 1). By means of a 30° inclination of the hand shape to the UV radiator the dose distribution can be considerably reduced (in the region of 1:3 to 1:4).

TABLE 1

| measuring point | 1 | 2 | 3 | 4 | 5 |
|---|---|---|---|---|---|
| Position 1 | | | | | |
| dose [mJ/cm$^2$] | 30 | 30 | 30 | 20 | 120 |
| | plus position 2 | | | | |
| dose [mJ/cm$^2$] | 100 | 100 | 30 | 30 | 200 |
| | plus position 3 | | | | |
| dose [mJ/cm$^2$] | 100 | 100 | 70 | 70 | >200 |

The same was found for the rear of the hand.

It is also an advantage in geometrically more complex molds, if more than one radiation source is used, where the radiation sources are arranged at different angles—dependent on the geometry—to the mold and/or if the mold performs a rotational movement by the radiation, whereby also in this case the angle of inclination of the mold to the radiation source can be varied if necessary during the radiation.

By means of the radiation sources 22, 23 or the radiation units 32 to 37 energy is transferred in the form of photons onto the photoinitiator, i.e. its molecules and in this way a radical fission of the molecules of the photoinitiator can be triggered. By means of the thereby resulting radicals as a result double bonds, which are in the latex molecules, for example in the main chain and/or in a side chain can be broken up according to the radical reaction mechanism and thus the crosslinking can be performed via initiator molecules or directly between the elastomer molecules.

In addition, according to an additional embodiment variant it is possible to add at least one auxiliary substance to the polymer dispersion and/or pre-emulsion. Said auxiliary substance can for example be a crosslinking auxiliary agent (co-crosslinking agent). For example, it is possible to have a thiol and/or a selenol as a crosslinking auxiliary means. Preferably, the thiol comprises two or more SH groups, whereby there is also an option of the so-called thiolene addition reaction, in order in this way to create crosslinking points in the polymer. In this way, an acceleration of the crosslinking reaction can be achieved. In addition to this crosslinking auxiliary means it is also possible to have additional crosslinking auxiliary means or additional auxiliary means, such as e.g. sensitizers, hydrogen donors, various process additives, such as e.g. stabilizers, antifoaming agents, dispensing agents, emulsifiers, coagulating agents, crosslinking chemicals, colorants and also fillers in the polymer dispersion or at least partly in the pre-emulsion, wherein said reagents are at least largely known from the prior art and at this point a person skilled in the art is referred to the relevant literature relating thereto, for example EP 0 856 294 A1 of the Applicant or to the publication "Kautschuktechnologie" (Rubber technology) (Röthemeyer/Sommer, Carl Hanser Verlag 2001).

The pre-emulsion or the pre-dispersion can be added at least partly to the polymer dispersion prior to the start of the pre-crosslinking reaction and/or the post-crosslinking. Similarly, it is possible to add the latter at least partly during the reaction of said polymer dispersion, for example add in small amounts, for example in droplets.

The radiation sources 22, 23 and the radiation units 32 to 37 can emit light in the already described spectral range, i.e. in particular between 200 nm and 550 nm or 250 nm and 475 nm or 275 nm and 400 nm.

With respect to the photoinitiator or possible mixtures of different photoinitiators reference is made at this point to the above explanations.

Both the radiation sources 22, 23 and the radiation units 32 to 37 as well as various agitators or possibly further components of the installation 1 can be connected operatively with a control and/or regulating device (not shown), such as e.g. a PC or generally a data processing system, so that if necessary an automization or a process sequence with variable reaction parameters can be performed fully automatically. For example in order to change the temperature, a corresponding heating and/or cooling device from the prior art can be arranged on or in the reactor(s) 19, 20.

It is also possible, to perform the pre-crosslinking and/or post-crosslinking at a pressure which is different from atmospheric pressure, for example at low pressure, it is also possible, to perform the crosslinking reaction under high pressure, and in addition at least one of the reactors 19, 20 or the post-crosslinking device 29 can be designed accordingly in this respect, i.e. for example vacuum-tight or also suitable to perform high pressure reactions, i.e. for example with reinforced walls.

The falling film reactor comprises on at least one surface suitable safeguards, such as e.g. a viewing window, in order to enable the penetration of electromagnetic radiation into the inside of the reactor or the reactors 19, 20. Furthermore, it is possible to form the latter from a UV transparent material, such as e.g. (quartz) glass or plastic, at least partly.

The radiation sources 22, 23 can however also be arranged on the inside of the falling film reactor, so that the polymer dispersion is exposed from the inside out.

Of course, it is possible for the pre-crosslinking and/or post-crosslinking of the latex or the lattice to be performed separately, i.e. independently of the additional production installation for latex products.

With regard to the used photoinitiators, the various auxiliary substances and their concentrations or proportions similarly as for the useable lattices and their proportion on the polymer dispersion reference is at this point made to the above explanations generally to avoid unnecessary repetition.

The solids used can be dissolved in a solvent within the scope of the invention and/or emulsified or dispersed in water.

It is also possible within the scope of the invention to perform a post treatment after the shaping, e.g. by heating, exposing or extruding.

The tearing resistances of the latex films produced within the scope of the invention can be in the region of 25 N/mm$^2$ to 30 N/mm$^2$, particularly for natural rubber, with an ultimate elongation of 800%-900%.

It is also possible to perform the radiation chemical crosslinking both continually and discontinually.

In the following several examples are described, which were performed within the scope of the invention. However, a description of all of the experiments carried out would exceed the scope of the present description. Therefore, the restriction to the following examples does not mean that the invention is restricted to the latter. Rather the range of the invention with respect to the used lattices or chemicals and their proportions is within the scope defined above.

The following materials or chemicals were used:

| Materials | Detailed description |
|---|---|
| NR latex | high ammonia NR latex/60% drc. |
| IR latex | Kraton ® IR 401 latex/60% drc. |
| Coagulation bath | CaCl$_2$ solution (10 wt. %) in water/additives: chalk, wetting agents |
| Lubricant bath | mixture of silicon, acrylate and polyurethane components |

| Chemical | Producer | Structure formula |
|---|---|---|
| Photoinitiators | | |
| Genocure DMHA | Rahn AG | |
| Irgacure 2959 | Rahn AG | |
| Genocure MBF | Rahn AG | |
| Lucirin TPO L | BASF | |
| Co-crosslinking agent | | |
| trimethylolpropane-tris-3-mercaptopropionate | Bruno Bock Thiochemicals | |

-continued
| | | |
|---|---|---|
| Pentaerythritol tetrakis-3-mercaptopropionate | Bruno Bock Thiochemicals | 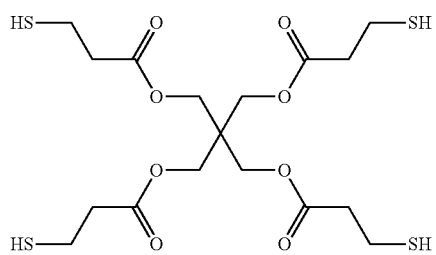 [SMILES: O=C(CCS)OCC(COC(=O)CCS)(COC(=O)CCS)COC(=O)CCS] |
| Other Chemicals | | |
| Tween 20 | Sigma-Aldrich | 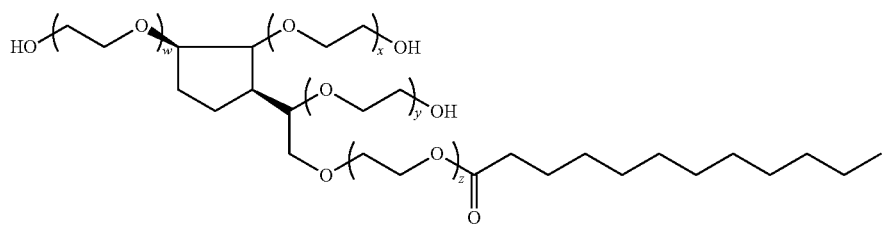 |
| Ralox LC ® | Solvadis | 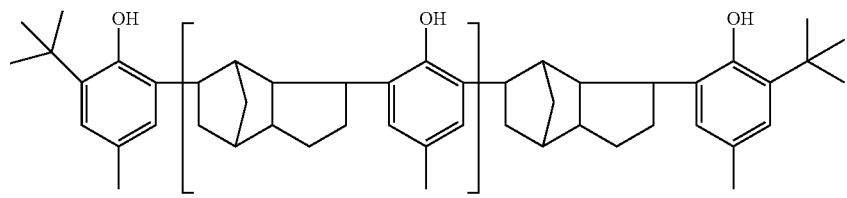 |
| Nekal BX | BASF | 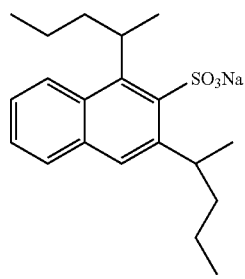 |
| Ascorbyl palmitate | Sigma-Aldrich | 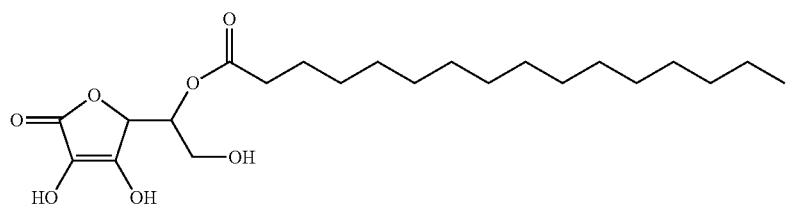 [SMILES: CCCCCCCCCCCCCCCC(=O)OC(CO)C1OC(=O)C(O)=C1O] |
| Linoleic acid | Sigma-Aldrich | 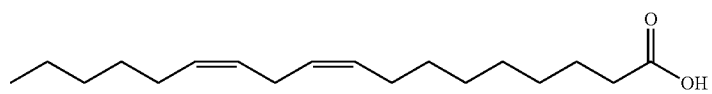 |
| α-Tocopherol | Sigma-Aldrich | 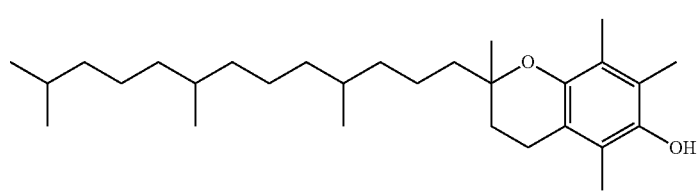 [SMILES: Cc1c(C)c2c(c(C)c1O)CCC(C)(CCCC(C)CCCC(C)CCCC(C)C)O2] |

EXAMPLE 1

UV Crosslinking of Natural Rubber (NR latex)

UV pre-crosslinking in film falling reactor:
(The abbreviation phr stands for parts per hundred parts rubber)

| Process parameter | |
|---|---|
| Radiator power output (Hg-high pressure lamp) [W] | 3000 |
| Number of exposure cycles | 2 |
| Photoinitiator | Genocure DMHA (0.5-1.0 phr) |
| Thiol-crosslinking agent | Tris-Thiol (1.0 phr) |
| Conveying speed [l/min] | 1.28 |
| layer thickness (falling film) [mm] | 0.45-0.6 |
| Solids content (latex) [drc.] | 40 |
| Cooling water pressure [bar] | 0.6 |
| Immersion: | |
| Storage period of liquid latex (pre-crosslinked) [days] | 0-1 |
| Stabilizer | Ralox LC (0.5 phr) |
| Drying temperature [° C.] | 120 |
| Drying period [min] | 20 |
| Subsequent doping prior to immersion | |
| Photoinitiator | Genocure DMHA (1.0-1.4 phr) |
| Thiol-crosslinking agent | Tetra-Thiol (1.0 phr) |
| Post-crosslinking | |
| Radiation dose [J/cm$^2$] | ~5 |

Figure 7:
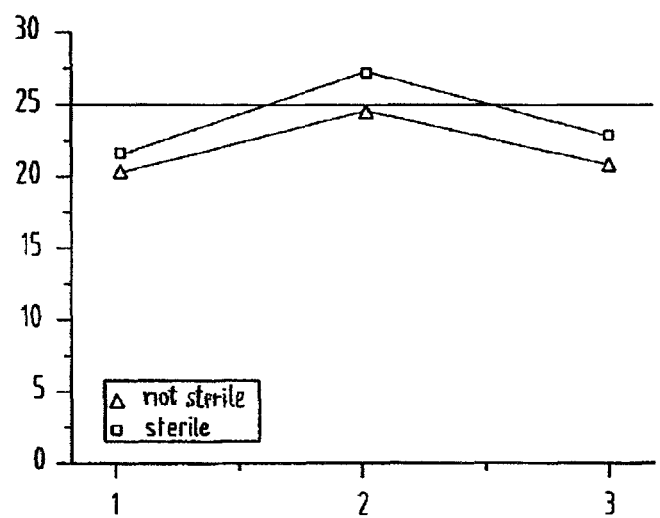
FIG. 7 shows a diagram of the tearing resistance of the elastomer as a function of the number of exposure cycles prior to a hot air ageing process.
Figure 8:
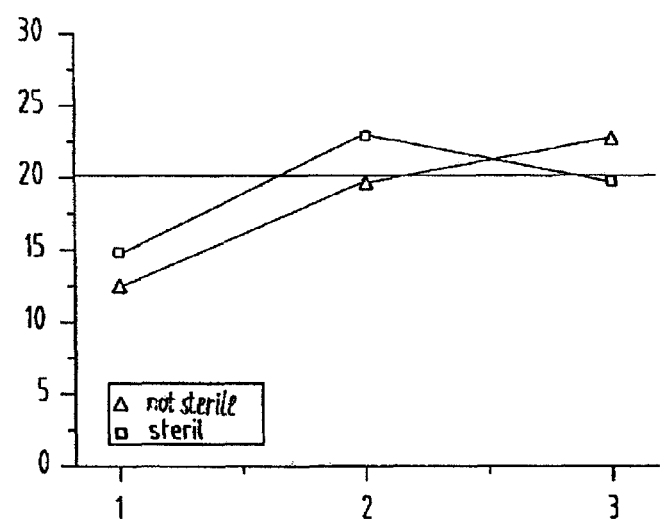
FIG. 8 shows a diagram of the tearing resistance of the elastomer as a function of the number of exposure cycles after a hot air ageing process.

During the crosslinking experiments NR latex was pre-cross-linked once, twice and three times at a radiation power of 3000 W, whereby after each exposure cycle latex samples were removed directly at the outflow valve. The results are shown in FIG. 7 and FIG. 8. Sterile samples (squares) were used and non-sterile samples (triangles) were measured. The tearing strengths in N/mm$^2$ (ordinates) are given in the Figs. relative to the number of exposures α-axes).

It can be concluded from the results that after pre-crosslinking twice a maximum in the mechanical strengths (crosslinking density is 0.28 mmol/cm$^3$) is achieved. In this case sterile, non-aged NR latex films (storage 7 days at 20° C.) have a tearing resistance of 26.5 N/mm$^2$, whereas after the hot air ageing the mechanical properties reduce to 22.0 N/mm$^2$.

With a single exposure cycle the crosslinking density (0.19 mmol/cm$^3$) is apparently too low, so that the subsequently immersed latex films have much lower tearing resistances (21 N/mm$^2$) associated with a worse ageing resistance (13-15 N/mm$^2$).

After a third exposure pass also a reduction in the tearing resistance is observed, as owing to over-crosslinking (crosslinking density is 0.49 mmol/cm$^3$) there is also a reduction in the mechanical strength, whereby the ageing resistance of an over-cross-linked NR latex film is largely higher compared to an under cross-linked one (one exposure cycle).

It was also found that crosslinking (pre-crosslinking and/or post-crosslinking) in an inert gas atmosphere (argon or nitrogen) after the second or third exposure cycle leads to an increase in the mechanical strengths of up to 5 N/mm$^2$.

Also drying the latex films at room temperature instead of at a raised temperature can lead to tearing resistances which are greater by up to 5 N/mm$^2$.

By means of the post-crosslinking lastly tearing resistances of up to 33 N/mm$^2$ could be achieved, wherein with a radiation dose of over 5 J/cm$^2$ the first degrading reactions could be observed in connection with air oxygen, which lead to a reduction of the tearing resistance.

EXAMPLE 2

UV Crosslinking of IR Latex

| UV-pre-crosslinking in falling film reactor | |
|---|---|
| Process parameter | |
| Radiator power output (Hg-high pressure lamp) [W] | 800 |
| Number of exposure cycles | 2 |
| Photoinitiator | Lucirin TPO L (0.5-1.0 phr) |
| Thiol-crosslinking agent | Tetra-Thiol (0.2-1.0 phr) |
| Conveying speed [l/min] | 1.28 |
| layer thickness (falling film) [mm] | 0.45-0.6 |
| Solids content (latex) [drc.] | 40 |
| Cooling water pressure [bar] | 0.6 |
| Immersion | |
| Storage period of liquid latex (pre-crosslinked) [days] | <1 |
| Ageing protection means[1] | Ralox LC (0.5 phr) |
| Residual moisture content [%] | <4 |
| Stabilizer | Nekal BX (1.25 phr) |
| Subsequent doping prior to immersion | |
| Photoinitiator | Lucirin TPO L (1.0-1.5 phr) |
| Thiol crosslinking agent | Tetra-Thiol (0.9-1.4 phr) |
| Post-crosslinking | |
| Radiation dose [J/cm$^2$] | ~4-13 |
| UV light source | Ga-doped Hg-radiator |

[1]optionally also 0.5 phr α-tocopherol
drc. . . . solids content

Generally, it should be noted that the power output of the radiators within the invention in the pre-crosslinking stage was between 300 W and 3000 W, in particular between 400 W and 1000 W, and in the post-crosslinking stage was between 2500 W and 4500 W, in particular between 3000 W and 3500 W, whereby it is an advantage, if the pre-crosslinking is performed at lower power. In particular with IR-lattices it is an advantage if the power output of the radiators of the pre-crosslinking does not exceed approximately 800 W, in order to obtain a better film formation. However, it should be noted that the radiator power output used can vary as a function of the geometry of the radiation installation from the values given by way of example.

Also the addition of surfactants in the pre-crosslinking stage, in particular surfactants with unsaturated C—C bonds, such as e.g. linoleic acid, can improve the film formation.

Furthermore, in particular with IR lattices the formation of a film by the addition of radical scavengers, such as e.g. ascorbyl palmitate (proportion 0.25 phr to 2 phr, in particular 0.5 phr to 1 phr), could be improved, so that also after drying tear-free films were obtained. Ascorbyl palmitate has the property of accumulating on the surface of the latex particles.

Owing to the allergy potential of the products and the economic efficiency of the method it is desirable to use as few chemicals as possible, but for high mechanical strengths (>20 N/mm$^2$) at least 1.0 phr Genocure DMHA and 1.0 phr tetra-thiol are preferred. Said tearing resistances could be improved in the absence of a stabilizer.

Ralox LC e.g. as a substituted BHT derivative collects in this case very effectively the initiator radicals in the post vulcanization, whereby the thiol-ene crosslinking is inhibited mainly at a low concentration (post doping of 1.0 phr Genocure DMHA and 1.0 phr tetra-thiol) of the process chemicals.

The use of Lucirin TPO-L as a photoinitiator has the advantage that by means of the absorption into the visible wavelength range on the one hand the radiation emission can be used efficiently for the post-crosslinking and on the other hand the long-wave light can penetrate into deeper layers, whereby a more homogenous crosslinking can be achieved over the latex film.

An improvement in the ageing resistance of UV crosslinked (pre-plus post-crosslinking) IR-latex films could be achieved with α-tocopherol (vitamin E), which occurs as an essential compound in the metabolism of the human body, and therefore is advantageous with respect to allergicological tolerance. The proportion of vitamin E can be between 0.2 phr and 1 phr.

The addition of vitamin E as a stabilizer is not restricted within the scope of the invention to IR-lattices. Vitamin E can be used in general for this purpose also in other lattices.

Vitamin E also has the advantage that it—surprisingly—does not inhibit or only slightly inhibits the thiol-ene reaction.

To improve the stability of the latex mixture for example a naphthyl sulfonate (Nekal BX; 0.2 phr-2.5 phr) is added, whereby the conveyability of the latex through smaller deposits in the installation 1 can be improved considerably.

Furthermore, it is an advantage if the level of pre-crosslinking is between 80% and 120%, in particular between 80% and 90%. In addition, the crosslinking density is determined to estimate the degree of crosslinking, as the latter is parameter to be determined rapidly, in order to characterize the reaction progress of the photochemical crosslinking.

The crosslink density provides more exact information about the crosslinking density and the average molecular weight of the polymer chains between the individual crosslinking points. In addition, the level of swelling of the of the UV crosslinked latex films is determined by means of the Flory Rehner method.

About 60 mg of the crosslinked latex film are swollen in 3 ml toluol for 48 h at 30° C. in a drying cabinet. Afterwards the films are filtered with a filter paper and immersed multiple times in diethyl ether. 30 s after removing the sample from the diethyl ether the latex film is weighed (+/−0.5 mg) and the sample is dried at 70° C. in the drying cabinet to a weight constant and weighed again. The crosslinking density is determined afterwards using the Flory Huggins interaction parameter between the solvent and polymer by the following equation system.

$$\overline{M_C} = -V_l \rho_P \frac{\phi_P^{1/3} - \frac{\phi_P}{2}}{\ln(1-\phi_P) + \phi_P + \chi_1 \phi_P^2}$$

$$\frac{1}{\phi_P} = 1 + \frac{W_s}{W_P}\frac{\rho_P}{\rho_s}$$

$\overline{M_c}$ average molar mass of the polymer chains between the crosslinking points
$V_l$ molar volume of the solvent
$\phi_P$ volume proportion of the polymer
$\chi_1$ Flory Huggins interaction parameter between the solvent and polymer
$W_s$ mass of the absorbed solvent
$W_P$ mass of the dry polymer
$\rho_s$ density of the solvent
$\rho_P$ density of the polymer The determination of the mechanical strengths of the latex films is performed in line with the ASTM standard D412-98a (Annu. Book ASTM Stand. 09.01 (2002)). The tearing resistance is used as a characteristic parameter. For the mechanical tensile testing 3-4 test bars (web width: 3 mm) are stamped out of a latex film. The thickness of the web is determined by means of a micrometer screw (arithmetical average value of 10 measurements) and entered manually into the measuring software. To evaluate the tearing resistance the arithmetical average value of the test bars of a sample are used.

To determine the resistance of the elastomers during the sterilization the latter were radiated by a Co60 source at a dose of 25 kGy. After receiving the gamma-sterilized latex films the tearing resistances are determined both before and after the hot air ageing (7 days at 70° C., in accordance with EN 455/2) by the tensile testing machine.

The exemplary embodiments show possible embodiment variants of the invention, whereby it should be noted at this point that the invention is not restricted to the embodiment variants shown in particular, but rather various different combinations of the individual embodiment variants are also possible and this variability, due to the teaching on technical procedure in the present invention, lies within the ability of a person skilled in the art in this technical field.

Finally, as a point of formality, it should be noted that for a better understanding of the structure of the pre-crosslinking device 18 and the post-crosslinking device 29, the latter and its components are not represented true to scale in part and/or have been enlarged and/or reduced in size.

LIST OF REFERENCE NUMERALS

1 Installation
2 Mixing step
3 Pre-vulcanization step
4 Chain immersion installation
5 Immersion
6 Edging
7 Wet leaching
8 Drying
9 Dry leaching
10 Powdering
11 Removal
12 Packaging
13 Quality control
14 Sterilization
15 Cleaning
16 Coagulant immersion
17 Drying
18 Pre-crosslinking device
19 Reactor
20 Reactor
21 Arrow
22 Radiation source
23 Radiation source
24 Container
25 Container
26 Container
27 Conveying device
28 Conveying device
29 Post-crosslinking device
30 Immersion mold
31 Immersion mold
32 Radiation unit
33 Radiation unit
34 Radiation unit
35 Radiation unit 36 Radiation unit
37 Radiation unit
38 Arrow
39 Arrow
40 Angle

The invention claimed is:

1. A method for producing a crosslinked elastomer by radiating a polymer dispersion of at least one crosslinkable polymer with electromagnetic radiation in the ultraviolet (UV light) and/or visible spectral range, wherein the crosslinking is performed in at least two stages as pre-crosslinking and post-crosslinking, and at least one first photoinitiator is added to the polymer dispersion to trigger the crosslinking reaction prior to the pre-crosslinking, wherein at least one second photoinitiator is added to the pre-crosslinked polymer dispersion prior to and/or during the post-crosslinking, and the post-crosslinking includes irradiation with electromagnetic radiation in the ultraviolet (UV light) and/or visible spectral range.

2. The method as claimed in claim 1, wherein the amount of the first photoinitiator is less than or equal to the amount of the second photoinitiator.

3. The method as claimed in claim 2, wherein the proportion of the first photoinitiator is between 0.2 phr and 5.0 phr.

4. The method as claimed in claim 2, wherein the proportion of the second is between 0.5 phr and 5.0 phr.

5. The method as claimed in claim 1, wherein the polymer dispersion is radiated at least twice in the pre-crosslinking.

6. The method as claimed in claim 1, wherein at least one of the first and second photoinitiators comprises 2-hydroxy-2-methyl-1-phenylpropanone, phenylglyoxylic acid methyl ester, 2,4,6-trimethylbenzoylphenylphosphinic acid ethyl ester, methylbenzoylformiate, 1-[4-(2-hydroxyethoxy)-phenyl]-2-hydroxy-methyl-1-propanone-1-one, 2-dimethylamino-2-(4-methylbenzyl)-1-(4-morpholine-4-ylphenyl)-butane-1-one, 2 methyl-1- [4-(methylthio)phenyl]-2-morpholinopropane-1-one, or 2,4,6-trimethylbenzoyl diphenylphosphine oxide.

7. The method as claimed in claim 1, wherein the pre-crosslinking is performed on a film comprising the polymer dispersion.

8. The method as claimed in claim 1, wherein for the post-crosslinking at least two radiation sources are used.

9. The method as claimed in claim 1, wherein the post-crosslinking is performed with a higher radiation dose than the pre-crosslinking.

10. The method as claimed in claim 9, wherein the post-crosslinking is performed with a radiation dose, which is between 150% and 500% of the radiation dose for the pre-crosslinking.

11. The method as claimed in claim 1, wherein at least one first co-crosslinking agent with at least one thiol group is included in the pre-crosslinking and/or at least one second co-crosslinking agent with at least one thiol group is included in the post-crosslinking.

12. The method as claimed in claim 11, wherein the amount of the first co-crosslinking agent is less than or equal to the amount of the second co-crosslinking agent.

13. The method as claimed in claim 12, wherein the proportion of the at least one first co-crosslinking agent is between 0.5 phr and 2.0 phr.

14. The method as claimed in claim 12, wherein the proportion of the at least one second co-crosslinking agent is between 0.5 phr and 2.5 phr.

15. The method as claimed in claim 11, wherein as a co-crosslinking agent trimethylolpropane tris-3-mercaptopropionate or pentaerythritol tetrakis-3-mercaptopropionate is used.

16. The method as claimed in claim 1, wherein at least one aging protection agent is added to the pre-crosslinked polymer dispersion prior to the post-crosslinking.

17. The method as claimed in claim 16, wherein the aging protection agent comprises vitamin E and/or a sterically hindered phenol.

18. The method as claimed in claim 1, wherein between the pre-crosslinking and the post-crosslinking, the pre-crosslinked elastomer is dried to a maximum residual moisture content of 6%.

19. The method as claimed in claim 1, wherein at least one surfactant with at least one photochemically active center is added to the polymer dispersion prior to the pre-crosslinking.

20. The method as claimed in claim 1, wherein for the radiation a mercury high pressure vapor lamp doped with gallium is used.

21. The method as claimed in claim 1, wherein the post-crosslinking is performed in an inert gas atmosphere.

22. A method for producing an immersion article from at least one latex, in particular a glove or a condom, in which a mold with an external contour, which corresponds to that of the immersion article to be produced, is immersed for a pre-specifiable period in an immersion bath containing the at least one latex, and afterwards the immersion article is hardened and/or dried, wherein the latex is crosslinked according to a method as claimed in claim 1.

23. The method as claimed in claim 22, wherein the shaping of the latex by immersing the mold into the immersion bath is performed between the pre-crosslinking and the post-crosslinking of the latex.

24. The method as claimed in claim 23, wherein the post-crosslinking is performed on the mold.

25. A glove made from a crosslinked elastomer, comprising a crosslinked elastomer produced by the method according to claim 1 and has a tearing resistance of at least 14 N/mm$^2$.

26. The method of claim 7, wherein the film has a maximum thickness of 2 mm.

27. The method of claim 19, wherein the photochemically active center of the at least one surfactant comprises a double bond.

28. The method of claim 1 wherein the at least one first photoinitiator is the same as the at least one second photoinitiator.

* * * * *